(12) United States Patent
Sharma et al.

(10) Patent No.: US 10,314,312 B2
(45) Date of Patent: Jun. 11, 2019

(54) SYNERGISTIC ANTIMICROBIAL COMPOSITION OF ZINC PYRITHIONE

(71) Applicant: Jubilant Life Sciences Limited, Uttar Pradesh (IN)

(72) Inventors: Vineet Sharma, Uttar Pradesh (IN); Ashutosh Agarwal, Uttar Pradesh (IN)

(73) Assignee: Jubilant Life Sciences Limited, Uttar Pradesh (IN)

( * ) Notice: Subject to any disclaimer, the term of this patent is extended or adjusted under 35 U.S.C. 154(b) by 0 days.

(21) Appl. No.: 15/321,413

(22) PCT Filed: Nov. 7, 2014

(86) PCT No.: PCT/IN2014/000713
§ 371 (c)(1),
(2) Date: Dec. 22, 2016

(87) PCT Pub. No.: WO2015/198338
PCT Pub. Date: Dec. 30, 2015

(65) Prior Publication Data
US 2017/0208815 A1    Jul. 27, 2017

(30) Foreign Application Priority Data
Jun. 27, 2014 (IN) .......................... 1725/DEL/2014

(51) Int. Cl.
| | |
|---|---|
| *A01N 43/40* | (2006.01) |
| *A01N 59/16* | (2006.01) |
| *A61Q 17/00* | (2006.01) |
| *A61K 8/27* | (2006.01) |
| *C09D 5/16* | (2006.01) |
| *A61K 8/49* | (2006.01) |
| *A61Q 5/00* | (2006.01) |
| *C09D 5/14* | (2006.01) |
| *C09D 131/02* | (2006.01) |

(52) U.S. Cl.
CPC ............ *A01N 59/16* (2013.01); *A01N 43/40* (2013.01); *A61K 8/27* (2013.01); *A61K 8/4926* (2013.01); *A61K 8/4933* (2013.01); *A61Q 5/006* (2013.01); *A61Q 17/005* (2013.01); *C09D 5/14* (2013.01); *C09D 5/1612* (2013.01); *C09D 5/1625* (2013.01); *C09D 131/02* (2013.01); *A61K 2800/58* (2013.01)

(58) Field of Classification Search
None
See application file for complete search history.

(56) References Cited

U.S. PATENT DOCUMENTS

| | | | |
|---|---|---|---|
| 5,696,169 A | 12/1997 | Otsu | |
| 5,939,203 A | 8/1999 | Kappock et al. | |
| 6,162,446 A * | 12/2000 | Hani | A01N 43/40 424/401 |
| 6,908,912 B2 | 6/2005 | Rioux et al. | |
| 7,026,308 B1 | 4/2006 | Gavin et al. | |
| 7,455,851 B1 | 11/2008 | Nelson et al. | |
| 8,119,168 B2 | 2/2012 | Johnson et al. | |
| 8,501,725 B2 | 8/2013 | Sianawati | |
| 8,691,726 B2 | 4/2014 | Sianawati et al. | |
| 2003/0223945 A1* | 12/2003 | Dalko | A61K 8/4926 424/70.1 |
| 2004/0005885 A1 | 1/2004 | Kato et al. | |
| 2004/0253194 A1* | 12/2004 | Rioux | A01N 43/40 424/70.11 |
| 2007/0190177 A1* | 8/2007 | Kling | A01N 59/16 424/641 |

FOREIGN PATENT DOCUMENTS

WO    WO-03/088965 A1    10/2003

OTHER PUBLICATIONS

Braga et al., "Crystal Polymorphism and Multiple Crystal Forms," Structure Bond (2009) 132:pp. 25-50. (Year: 2009).*
Reeder et al. article, "the antifungal mechanism of action of zinc pyrithione", British Journal of Dermatology, 2011, pp. 9-12. (Year: 2011).*
Nagashree et al., "Synthesis, Characterization, and Antimicrobial Activity of Methyl-2-aminopyridine-4-carboxylate Derivatives," Hindawi Publishing Corporation, Journal of Chemistry, vol. 23, pp. 1-6). (Year: 2013).*
International Search Report and Written Opinion for PCTT/IN2014/000713, dated Jan. 29, 2015, 5 pages.
Schwartz, Jr., "Zinc Pyrithione: A Topical Antimicrobial with Complex Pharmaceutics", J. Drugs Dermatol., Feb. 2016; 15(2): 140-4, 1 page.
G. Imokawa, et al., "Antimicrobial Effect of Zinc Pyrithione", J. Soc. Cosrnet. Chem., 33; 27-37; Jan./Feb. 1982; 11 pages.
"Zinc Pyrithione", https://archive.epa.gov/pesticides/reregistration/web/html/index-292.html; Feb. 2016; 2 pages.
"Zinc Omadine™ 48% Dispersion Antimicrobial", Lonza—Adhesives & Sealants; Prospector; https://www.ulprospector.com/en/eu/Adhesives/Detail/6216/109004/ZINC-OMADINE-48-Dispersion-Antimicrobial; 2 pages, printed Jun. 10, 2018.
M. Qui, et al., "Zinc Ionophores Pyrithione inhibits Herpes Simplex Virus Replication Through Interfering with Proteasome Function and NF-κB Activation"; Antiviral Research, www.elsevier.com/locate/antiviral; 100; 2013; pp. 44-53.

* cited by examiner

*Primary Examiner* — Ernst V Arnold
*Assistant Examiner* — Kyung S Chang
(74) *Attorney, Agent, or Firm* — Blank Rome LLP

(57) ABSTRACT

The present invention discloses synergistic antimicrobial composition comprises zinc pyrithione and a zinc salt of pyridine carboxylic acid.

22 Claims, No Drawings

SYNERGISTIC ANTIMICROBIAL COMPOSITION OF ZINC PYRITHIONE

RELATED APPLICATIONS

This application is a national phase of PCT/IN2014/000713, filed on Nov. 7, 2014, which claims the benefit of India 1725/DEL/2014, filed on Jun. 27, 2014. The entire contents of those applications are incorporated herein by reference.

FIELD OF THE INVENTION

This invention relates to a synergistic antimicrobial composition comprising zinc pyrithione and zinc salt of pyridine carboxylic acid. More particularly, the present invention provides various personal care, paint, coating and industrial formulations comprising synergistic antimicrobial composition comprising zinc pyrithione and zinc salt of pyridine carboxylic acid.

BACKGROUND OF THE INVENTION

The antimicrobial compounds are widely used in bacterial remedies in various industrial processes, drinking water, waste management, daily use cosmetics, and furniture. These have applications in water treatment, personal care products, paints and coatings, wood preservation, food and beverages preservations. These are widely used to control the growth of pathogenic microorganisms or to eliminate them from inanimate objects, surfaces or intact skin.

One of the most widespread uses of antimicrobials is in personal care formulations, antidandruff shampoos wherein they are formulated (as actives/preservatives) in both leave-on and rinse-off preparations. They are also used as biocides in anti-fouling paints, which is a specialized coating applied to the hull of a ship or boat to slow the growth of organisms that attach to the hull and can affect a vessel's performance and durability.

Commonly used antimicrobial compounds are quaternary ammonium compounds, biguanides, alcohols, aldehydes, ethylene oxide, anionic agents, organic acids, metallic salts, isothiazolinones, peroxides, chlorine compounds and halogens. These compounds are sometimes included in liquid coating compositions that are applied to a substrate and that become dry films. It is desirable that such dry films control surface fungi and algae and also present as little adverse effect as possible on health and the environment.

In antifouling paints the most commonly used biocides are Irgarol 1051, diuron, Sea-nine 211, dichlofluanid, chlorothalonil, zinc pyrithione, (2,3,3,6-tetrachloro-4-methylsulfonyl) pyridine (TCMS), 2-(thiocyanomethylthio)benzothiazole (TCMTB) and zineb. All these agents have different mechanism of action and have different preferred end use. Since the partial ban on the application of organotin biocides, especially tributyltin (TBT) in antifouling paints for small marine vessels, these new generation of surrogate antifouling biocides have been increasingly used. These surrogate biocides are often applied in conjunction with copper (Cu) compounds such as cuprous oxide, copper thyocyanate or metallic copper to control Cu-resistant fouling organisms. Of these, zinc pyrithione has been widely used as an antifungal and antibacterial agent.

Zinc pyrithione as an antimicrobial compound is used around the world in a variety of applications including antifouling paints, building products, plastics, polyurethane products, textiles and antidandruff shampoos. Zinc pyrithione is approved for over-the-counter topical use in the United States as a treatment for dandruff. It is the active ingredient in several anti-dandruff shampoos. It is also used as a preservative in personal care products, in building products, plastics and polyurethane products, as well as biocide in textiles.

Although zinc pyrithione is known as an excellent antimicrobial component with broad range of activity against wide variety of microorganisms, there is a continuous demand for an effort to develop advanced zinc pyrithione containing antimicrobial compositions of high antimicrobial efficacy with the reduced blending amount of zinc pyrithione and multiple add-on benefits as per the end use. When used in personal care applications, it is desirable that the formulation should have improved scalp and/or hair conditions and reduced inflammation. Similarly, when used in paints and coatings, it is desirable that there should be low leaching rate of biocide, prevention and/or inhibition of in-can discolouration of composition and low environmental toxicity for various paint and coating applications. It is also desirable that the final product should be effective even at lower concentration of the active.

The prior art is replete with various references which disclose various methods to increase the efficacy of pyrithione salt by using them either in various combinations or formulating them appropriately so that their delivery at the required site increases.

US Publication No. 2004/0058855 describes a method of delivering excess zinc to eukaryotic cells (fungi, yeast) through zinc ionophoric material along with a zinc containing material to inhibit the cell metabolism. The invention also relates to a method of treating microbial infections on the skin or scalp by delivering excess zinc and thus provide improved anti-fungal/anti-dandruff activity.

U.S. Pat. No. 5,939,203 discloses discoloration prevention in pyrithione-containing coating compositions by using zinc oxide along with zinc pyrithione. U.S. Pat. Nos. 6,908,912 and 7,455,851 disclose a stable, soluble, antimicrobial composition where insoluble metal salts of pyrithione in combination with a zinc source (zinc salts, -oxides, -hydroxides, -borates, -sulfates, -chlorides etc.) were solubilised in alkanolamines. These reported compositions deliver higher concentration of pyrithione and zinc ions to an application (in-can preservatives and metalworking fluids) and thus provide enhanced biocidal efficacy against microorganisms and bio-films. U.S. Pat. No. 7,026,308 describes a topical scalp care composition with enhanced anti-dandruff efficacy containing zinc pyrithione, a metal ion source and strong chelating agent.

However, the antimicrobial compositions disclosed in these patents readily form insoluble precipitates as the concentrations of pyrithione and the zinc source are increased to develop a concentrated biocidal composition. These insoluble precipitates reduce the effectiveness of the composition as an antimicrobial agent and do not provide aesthetic benefits to the products.

U.S. Pat. No. 8,501,725 discloses a synergistic combination of flumetsulam or diclosulam with zinc pyrithione. U.S. Pat. No. 8,691,726 discloses synergistic combination of a glyphosate compound and zinc pyrithione. These combinations have greater activity than would be observed for the individual antimicrobial compounds.

U.S. Pat. No. 8,119,168 describes personal care compositions containing zinc oxide and zinc pyrithione, a detersive surfactant, sodium bicarbonate and water. The pH of the composition is greater than 7 and the zinc oxide has a relative zinc lability of greater than 15%.

Khattar and Salt in Journal of Antimicrobial Chemotherapy, 1993, 175-177 reported the enhancement in antibacterial activity of pyrithione against *Klebsiella pnenmoniae* bacteria specifically in combination with zinc chloride.

Although zinc pyrithione is known as an excellent antimicrobial component with broad range of activity against wide variety of microorganisms, but there is a continuous demand for an effort to develop additional combinations of antimicrobial compounds with relatively low impact on health and/or the environment. Accordingly, what is needed in the art is antimicrobial composition that is highly efficacious against variety of microorganisms and bio-films at reduced active concentration, does not have environmental and toxicological effects and can provide multiple benefits for various personal care, paint, coating, industrial applications like improved scalp and/or hair conditions, reduced inflammation, low leaching rate of biocide and prevention or inhibition of in-can discolouration of composition.

The present invention provides novel composition of zinc pyrithione with zinc salt especially zinc salt of pyridine carboxylic acid salt. The combination produces synergistic effect as compared to zinc pyrithione when used alone or pyridine carboxylic acid salts alone. The combination also shows reduced leaching of the biocide from paint composition. The present invention also provides various personal care, paint, coating and industrial compositions comprising such synergistic composition. These compositions have enhanced efficacy and have widespread scope in end use.

SUMMARY OF THE INVENTION

It is a principal object of the present invention, to provide a synergistic antimicrobial composition, comprising zinc pyrithione and zinc salt of pyridine carboxylic acid, their tautomeric forms, isomers, polymorphs, salts and solvates and mixtures thereof.

It is another object of the present invention, to provide synergistic antimicrobial composition, comprising zinc pyrithione and zinc salt of pyridine carboxylic acid, their tautomeric forms, isomers, polymorphs, salts and solvates and mixtures thereof, wherein zinc pyrithione is present in an amount ranging from 0.01-50% w/w and zinc salt of pyridine carboxylic acid is present in an amount ranging from 0.001-30% w/w.

It is yet another object of the present invention, to provide synergistic antimicrobial composition, comprising zinc pyrithione and zinc salt of pyridine carboxylic acid, their tautomeric forms, isomers, polymorphs, salts and solvates and mixtures thereof, wherein the said composition is present in the form of or is incorporated into various personal care, paint, coating and other industrial formulations.

It is another object of the present invention, to provide an antimicrobial personal care formulation, comprising water; surfactant from the group consisting of anionic surfactant, cationic surfactant, non-ionic surfactant, amphoteric surfactants or a combination thereof; zinc pyrithione, in an amount of from 0.01% to 2.0%, based upon the weight of the composition, and zinc salt of pyridine carboxylic acid at a concentration of from 0.001% to 5%, based upon the weight of the composition.

It is another object of the present invention, to provide an antimicrobial coating and/or a paint formulation comprising water; a base medium comprising resin selected from the group consisting of vinyl, alkyl, epoxy, acrylic, polyurethane, polyester resins, and combinations thereof; zinc pyrithione, in an amount of from 0.01% to 5.0% based upon the weight of the composition, and zinc salt of pyridine carboxylic acid at a concentration of from 0.001% to 10% based upon the weight of the composition.

It is another object of the present invention, to provide a coated substrate wherein the said substrate is coated with a synergistic antimicrobial composition comprising zinc pyrithione and zinc salt of pyridine carboxylic acid, their tautomeric forms, isomers, polymorphs, salts, solvates and mixtures thereof.

It is also one object of the present invention, to provide an antidandruff hair care composition, comprising synergistic antimicrobial composition comprising zinc pyrithione and zinc salt of pyridine carboxylic acid, their tautomeric forms, isomers, polymorphs, salts, solvates and mixtures thereof.

Other aspects of the invention will be set forth in the description which follows, and in part will be apparent from the description, or may be learnt by the practice of the invention.

DETAILED DESCRIPTION OF THE INVENTION

The use of synergistic combinations of compounds for antimicrobial compositions can broaden potential markets, reduce use concentrations and costs, and reduce waste. In some cases, commercial antimicrobial compounds cannot provide effective control of microorganisms, even at high use concentrations, due to weak activity against certain types of microorganisms, whereas in other cases, like pyrithione biocides, to control the growth of a wider range of organisms effectively higher concentrations of pyrithione salts are required but, the useful amount of pyrithione or its salts that can be added to a commercial product is limited to a lesser extent due to toxicological, environmental and economic considerations.

The present invention permits the use of reduced amount of the metal pyrithione as primary biocide, in conjunction with metal salt of pyridine carboxylic acid, thereby providing an antimicrobial composition that is less expensive to produce and that possesses the characteristic of synergistic antimicrobial effectiveness against variety of microorganisms.

It has been surprisingly found in accordance with the present invention that the combination of zinc pyrithione and zinc salt of pyridine carboxylic acid show effective synergistic antimicrobial efficacy at lower concentration of actives relative to pyrithione or other combinations of antimicrobial compound thereby making it more efficacious and environment friendly composition. In addition, the zinc salt of pyridine carboxylic acid as a substrate also functions as nutrient source (for e.g Zinc Nicotinate as Vitamin B3), hence helps in improved scalp and/or hair conditions, hair restoration effect and reduced inflammation.

The composition of the present invention also surprisingly exhibited lower leaching rate of the zinc pyrithione or zinc salt from the paints and coatings.

As used herein, the following terms have the designated definitions, unless the context clearly indicates otherwise.

The term "antimicrobial compound" refers to a compound capable of inhibiting the growth of or controlling the growth of microorganisms; antimicrobial compounds include bactericides, bacteristats, fungicides, fungistats, algaecides and algistats, depending on the dose level applied, system conditions and the level of microbial control desired.

The term "personal care formulation" as used herein refers to various toiletries and cosmetic preparation used for general health and hygiene and grooming. Examples of personal care formulation includes hair care and skin care formulations but are not limited to shampoos, creams, lotions, sprays, tonics, gels, paste, mousses, serums, oils, solid or liquid soaps, shower gels and hair conditioning and/or moisturizing, hair strengthening, hair drying, hair colouring, hair shaping and hair dyeing compositions, face lotions, body lotions, moisturizing compositions, sun protection compositions, makeup preparations, shaving preparations and aids, hand cleansers, water-less hand sanitizer and facial cleansers, powders and the likes.

The term "surfactant" as used herein refers to substances which lower the surface tension of the medium in which it is dissolved, and/or the interfacial tension with other phases, and accordingly, is positively adsorbed at the liquid/vapour and/or at other interfaces. A surfactant tends to reduce the surface tension of a liquid in which it is dissolved. Surfactants have a hydrophobic (water repellent) part and a hydrophilic ('water loving') part. The hydrophobic part consists of an uncharged carbohydrate group that can be straight, branched, cyclic or aromatic. Depending on the nature of the hydrophilic part the surfactants are classified as anionic, cationic, non-ionic, or amphoteric.

The term "surfactant system" as used herein refers to one or more surfactants selected form anionic surfactant, cationic surfactant, non-ionic surfactant, amphoteric surfactants or a combination thereof.

The term "anionic surfactant" as used herein refers to those surfactants where the hydrophilic part consists of a negatively charged group like a sulphonate, sulphate or carboxylate the surfactant. Examples of anionic surfactant include but are not limited to sodium, potassium or ammonium salts of long chain sulphates having carbon chain lengths 6-14, preferably sodium lauryl sulfate (SLS), sodium laureth sulfate (SLES), triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, ammonium lauryl sulfate, ammonium laureth sulfate, lauric monoglyceride sodium sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, monoethanolamine lauryl sulfate, sodium tridecyl benzene sulfonate, sodium dodecyl benzene sulfonate, sodium cocoyl isethionate, amino acid derived surfactants and combinations thereof.

The term "cationic surfactant" as used herein refers to those surfactants where the hydrophilic part consists of a positively charged group. Examples of cationic surfactant include but are not limited to cetyl pyridinium chloride, stearyl pyridinium chloride, methyl or ethyl cetyl pyridinium chloride, aralkyl ammonium halides such as benzyl triethyl ammonium chloride, benzalkonium chloride, cetalkonium chloride, benzethonium chloride, lauryltrimethyl ammonium halide, cetrimonium halide or cetyltrimethyl ammonium halide, glycidyltrimethylammonium halide, tallowtrimethyl ammonium chloride, cocotrimethyl ammonium chloride, vitamin B6 hydrochloride, behenyltrimethyl ammonium chloride (BTAC), octyltrimethyl ammonium chloride, octyldimethylbenzyl ammonium chloride, decyldimethylbenzyl ammonium chloride, stearyldimethylbenzyl ammonium chloride, didodecyldimethyl ammonium chloride, dioctadecyldimethyl ammonium chloride, dipalmitoylethyldimethyl ammonium chloride and combinations thereof.

The term "non-ionic surfactant" as used herein refers those surfactants where the hydrophilic part is not charged. Examples of non-ionic surfactant include, but are not limited to Lamesoft PO65, polyoxyethylene (20) sorbitan monooleate (Tween 80), polyoxyethylene (20) sorbitan monolaurate (Tween 20), ethoxylated sorbitan monolaurate (Crillet 180) and combinations thereof.

The term "amphoteric surfactant" as used herein refers to those surfactants wherein hydrophilic part can be either positively or negatively charges depending on the pH of the solution. They can act as anionic surfactant in an alkaline solution or as cationic surfactant in an acidic solution. Examples of amphoteric surfactant include but are not limited to cocamidopropyl betaine (CAPB) or cocamide DEA and combinations thereof.

The term "suspending agents" are as used herein refers to insoluble particles dispersed in a vehicle and help to reduce the sedimentation rate of particles in suspension. The term "dispersants" as used herein are substances which facilitate the dispersion of aggregates and improve the kinetic stability of the particles.

The term "rheology modifiers" as used herein refers to compounds/polymers which alter the thickness or viscosity of the system. Throughout the specification, these terms have been used interchangeably. Examples of dispersants and/or rheology modifier and/or suspending agent as used herein include but are not limited to sodium and potassium salts of alkyl-aryl sulfonic acids and/or polymerized alkyl-aryl sulfonic acids and/or formaldehyde complexes, synthetic silicates, castor oil based thixotropes and organic thixoptropes, carboxymethylcellulose, organoclays, synthetic clays, polymers of acrylic acid cross-linked with polyalkenyl ethers or divinyl glycol, Stepan TAB-2, Stepan SAB-2, Carbopol ETD 2020, Carbopol Aqua SF-1, Carbopol Ultrez 20, Rheocare TTA, Rheocare C Plus, xanthum gum, dehydroxanthan gum like Amaze XT, methyl hydroxyethylcellulose like Structure Cell 12000 and combinations thereof. Sodium and potassium salts of alkyl-aryl sulfonic acids and/or polymerized alkyl-aryl sulfonic acids and/or formaldehyde complexes is selected from but not limited to Tytan series, Tysperse series, DARVAN Series, DEMOL Series, DAXAD Series, TAMOL Series, HAROL Series, LOMAR Series and the likes; synthetic silicates is selected from but not limited to sodium aluminium silicate, magnesium aluminum silicates and the likes; organoclays such as Claytone, Tixogel and the likes; synthetic clay such as Veegum, Laponite and the likes.

The term "suitable solvent" as used herein refers to cosmetically acceptable water and water miscible solvents such as glycol, polyol, glycol ethers, lactams and the like. Exemplary water miscible glycols/polyol/glycol ethers include but are not limited to propylene glycol, glycerol, sorbitol, PEG 400, polyglycol 500 DME, ethylene glycol monoethyl ether, diethylene glycol monomethyl ether, diethylene glycol monoethyl ether, diethylene glycol dimethyl ether (diglyme), triethylene glycol dimethyl ether (triglyme), tetraethylene glycol dimethyl ether (tetraglyme) and combinations thereof; exemplary lactams include but are not limited to 2-pyrrolidone, N-methyl pyrrolidone (NMP), polyvinylpyrrolidone (PVP) and combinations thereof.

The term "paint and coating formulations" as used herein refers to but not limited to indoor and outdoor household paints, industrial and commercial paints and marine antifouling paints.

In addition to the antimicrobial component, a "paint formulation" typically contains a resin, a pigment and various optional additives which have a favourable influence on the viscosity, wetting power and dispersibility, stability to freezing and electrolytes and on the foaming properties. These optional additives includes thickening agent(s) and/or viscosity modifiers, wetting agents, defoamers and defreezing agents (freeze-thaw stabilizers) and the like, as are well known in the art. The resin is preferably selected from the group consisting of vinyl, alkyl, epoxy, acrylic, polyurethane and polyester resins and combinations thereof. The resin is preferably employed in an amount of between about 20% and about 80% based upon the weight of the paint or paint base. If a marine paint is being fabricated, the paint preferably contains a swelling agent to cause the paint to gradually "slough off" in its marine environment, thereby causing renewed biocidal efficacy of newly exposed biocide at the surface of the paint in contact with the water medium of the marine environment. Illustrative swelling agents are naturally occurring or synthetic clays, such as kaolin, montomorillonite and bentonite, clay mica (muscovite) and chlorite (hectonite) and the like. In addition to clays other swelling agents, including natural or synthetic polymers, such as the commercially available POLYMERGEL have been found to be useful in the compositions of the present invention to provide the desired "sloughing off" effect. Swelling agents can be used singly or in combination. The total amount of optional additives is preferably no greater than 20% by weight, more preferably between about 1% to about 10% by weight, based upon the total weight of the paint formulation.

Illustrative, thickening agents include cellulose 30 derivatives, for example methyl, hydroxyethyl, hydroxypropyl and carboxymethyl cellulose, poly(vinyl alcohol), poly (vinylpyrolidone), poly(ethyleneglycol), salts of poly(acrylic acid), salts of acrylic acid/acrylamide copolymers and Attagel Series.

Suitable wetting and dispersing agents include sodium polyphosphate, salts of low molecular weight poly(acrylic acid), salts of poly(ethane sulfonic acid), salts of poly (vinyl phosphonic acid), salts of poly(maleic acid) and salts of copolymers of maleic acid with ethylene, 1 olefins 3 to 18 carbon atoms and/or styrene.

In order to increase the stability to freezing and electrolytes there may be added to the paint composition various monomer 1,2-diols for example glycol, propylene glycol (1,2) and butylene glycol 1,2) or polymers thereof or ethoxylated compounds. For example reaction products of ethylene oxide with long-chain alkanols, amines, alkyl phenols, poly (propyleneglycol) or poly(butylene glycol) or a combination thereof, or the likes.

The minimum temperature of film formation (white point) of the paint composition may be reduced by adding solvents, such as ethyl glycol acetate, ethyl diglycol acetate, butyl diglycol acetate, benzene or alkylated aromatic hydrocarbons. As defoaming agents the suitable examples are 2,2,4-trimethylpentane-1,3-diolmonoisobutyrane, poly(propylene glycol) and polysiloxanes. Optionally other biocides can additionally be incorporated into the paint formulations of the present invention. Useful optional solvents include methylisobutylketone (MIBK), xylene, ethyl benzene, methanol, and combinations thereof.

The term "microorganism" includes, for example, fungi (such as yeast and mold), bacteria and algae. The following abbreviations are used throughout the specification: ppm=parts per million by weight (weight/weight), mL=milliliter, ATCC=American Type Culture Collection, ZOI=zone of inhibition, av=average, MIC=minimum inhibitory concentration, ZPTO=Zinc pyrithione. Unless otherwise specified, temperatures are in degrees centigrade (° C.), and references to percentages are by weight (wt %). Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present.

In accordance with one of the embodiment of the present invention, there is provided a synergistic antimicrobial composition comprising zinc pyrithione and zinc salt of pyridine carboxylic acid, their tautomeric forms, isomers, polymorphs, salts and solvates and mixtures thereof.

In accordance with one other embodiment of the present invention, there is provided a synergistic antimicrobial composition, comprising zinc pyrithione and zinc salt of pyridine carboxylic acid wherein zinc pyrithione is present in an amount ranging from 0.01-50% w/w, preferably in an amount ranging from 0.5-45% w/w, more preferably in an amount ranging from 5-45% w/w and most preferably in an amount ranging from 10-40% w/w.

In accordance with one other embodiment of the present invention, there is provided a synergistic antimicrobial composition, comprising zinc pyrithione and zinc salt of pyridine carboxylic acid wherein zinc salt of pyridine carboxylic acid is present in an amount ranging from 0.001-30% w/w, preferably in an amount ranging from 0.5-30% w/w, more preferably in an amount ranging from 2-25% w/w and most preferably in an amount ranging from 5-20% w/w.

In accordance with one other embodiment of the present invention, there is provided a synergistic antimicrobial composition, comprising zinc pyrithione and zinc salt of pyridine carboxylic acid wherein the weight ratio of zinc salt of pyridine carboxylic acid to the zinc pyrithione is in the range from about 1:300 to about 50:1

In accordance with another embodiment of the present invention, there is provided a synergistic antimicrobial composition as described hereinabove, wherein the zinc salt of pyridine carboxylic acid is selected from the group comprising zinc salts of 2-pyridinecarboxylic acid; 3-pyridinecarboxylic acid; 4-pyridinecarboxylic acid; 2,3-pyridinedicarboxylic acid; 2,6-pyridinedicarboxylic acid; 2,5-pyridinedicarboxylic acid; 3,5-pyridinedicarboxylic acid, their tautomeric forms, isomers, polymorphs, salts and solvates and mixtures thereof.

In accordance with a preferred embodiment of the present invention, there is provided a synergistic antimicrobial composition, comprising zinc pyrithione and zinc salt of pyridine carboxylic acid wherein the zinc salt of pyridine carboxylic acid is selected from 2-pyridinecarboxylic acid and 3-pyridinecarboxylic acid, their tautomeric forms, isomers, polymorphs, salts and solvates and mixtures thereof.

In accordance with one embodiment of the present invention, there is provided an antimicrobial composition comprising metal pyrithione and metal salt of pyridine carboxylic acid. This antimicrobial composition is used into various personal care, paint, coating and other industrial formulations.

In accordance with another embodiment of the present invention, the synergistic antimicrobial composition further comprises one or more additional pyrithione(s). The pyrithione is selected from the group comprising sodium pyrithione, silver pyrithione, copper pyrithione, iron pyrithione, aluminum pyrithione, calcium pyrithione, potassium pyrithione, magnesium pyrithione, barium pyrithione, and combinations thereof.

The metal salt of pyridine carboxylic acid is selected from the group comprising zinc, copper, sodium, silver, iron, aluminium, calcium, potassium, magnesium, barium salt of pyridine carboxylic acid.

The metal pyrithione(s), in particular, zinc pyrithione of the present invention may have any particle form suitable for use in a composition for personal care, paints, coatings and other industrial applications. For example, the pyrithiones may be in the form of amorphous or crystalline particles having a range of different particle sizes.

The zinc pyrithione may, for example, be in the form of particles having an average size of particle ranging from 0.1 microns to about 20 microns. The desired particle size may be achieved by methods well known to the person skilled in the art. Suitable methods for determining particle size are also described in the prior art.

The metal pyrithiones may be made up of one particulate form or two or more different particulate forms. Suitable particulate forms for the metal pyrithione include platelets and needle-shaped particles.

In accordance with one embodiment, the synergistic antimicrobial composition of the present invention is incorporated into various personal care, paint, coating and industrial formulations. The amount of synergistic antimicrobial composition of the present invention which is incorporated into various formulations depends on the type and the exact nature of the material used. A preferred amount is from about 0.001% to about 10% by weight of the total formulation, preferably from about 0.05% to about 4% by weight, most preferably between 0.1% and 2% by weight.

In accordance with one embodiment, the personal care formulation is selected from but not limited to various personal care formulations and medicaments for the treatment of the skin and/or the hair, like shampoos, creams, lotions, sprays, tonics, gels, paste, mousses, serums, oils, solid or liquid soaps, shower gels and hair conditioning and/or moisturizing, hair strengthening, hair drying, hair colouring, hair shaping and hair dyes, face lotions, body lotions, moisturizers, sun protection compositions, makeup preparations, shaving preparations and aids, hand cleansers, water-less hand sanitizer and facial cleansers, powders and the likes, anti dandruff and/or anti fungal hair care formulation.

In accordance with one embodiment of the present invention, there is provided an antimicrobial personal care formulation comprising water; surfactant from the group consisting of anionic surfactant, cationic surfactant, non-ionic surfactant, amphoteric surfactants or a combination thereof; zinc pyrithione, in an amount of from 0.01% to 2.0%, based upon the weight of the composition, and zinc salt of pyridine carboxylic acid at a concentration of from 0.001% to 5%, based upon the weight of the formulation.

In accordance with one other embodiment of the present invention, the antimicrobial personal care formulation further comprises one or more components selected from a solubilizer, dispersant and/or a rheology modifier and/or a suspending agent, diluents, humectants, pH regulators, preservatives, perfumes, skin active agents and/or scalp modifiers, hair growth and/or hair loss preventive agents, sunscreens, UV absorbers, vitamins, herbal extracts and the likes.

In accordance with a preferred embodiment, the antimicrobial composition is used for anti dandruff hair care formulations.

In accordance with yet another embodiment of the present invention, there is provided an antimicrobial coating and/or paint formulation comprising water; a base medium comprising a resin selected from the group consisting of vinyl, alkyl, epoxy, acrylic, polyurethane, polyester resins, and combinations thereof; zinc pyrithione, in an amount of from 0.01% to 5.0% based upon the weight of the composition, and zinc salt of pyridine carboxylic acid at a concentration of from 0.001% to 10% based upon the weight of the formulation.

In accordance with an embodiment of the invention, the industrial formulation is selected from but not limited to various coatings, paints, varnishes, stains, renders, latices, polymer dispersions, adhesives, cleaning products, lignosulfonates, chalk slurries, mineral slurries, ceramic masses, adhesives, sealants, products containing casein, products containing starch, bitumen emulsions, surfactant solutions, motor fuels, cleaning products, pigment pastes and pigment dispersions, inks, lithographic fluids, thickeners, toiletries, water circuits, liquids associated with paper processing, liquids associated with leather making, liquids associated with textile production, drilling and cutting oils, hydraulic fluids, cooling lubricants and in can preservative.

The paint formulation of the present invention may be used as paint for natural or synthetic materials, for example wood, paper, metals, textiles and plastics. It is particularly suitable as an outdoor paint, and is excellent for use as a marine paint. The coating compositions of the present invention are suitably applied to a substrate, such as a wood, plastic or metal substrate, and allowed to dry to form a dry coating. The dry film formed by coating and drying the coating composition of the present invention onto a substrate exhibits excellent resistance to the growth of fungus and algae.

However, the paint formulations rich in hydrophilic components tend to cause relatively soluble antimicrobial additives to leach out of the formulation, thus providing short-term antimicrobial protection at the expense of longer-term antimicrobial protection due to this leaching effect. In accordance with the present invention, the antimicrobial composition comprising zinc pyrithione, in combination with zinc salt of pyridine carboxylic acid possess low leaching rate and thus provides an excellent long-lasting antimicrobial protection in dry paint films made using paint formulations containing high levels of hydrophilic components.

The antimicrobial composition of the present invention are suitable for a variety of uses as a biologically active agent or as a preservative, such as in hair care and skin care formulations, in medical formulation, in fabric care compositions, in cutting oils and coolant systems, paints, coatings, adhesives, caulks, sealants, wet-state preservatives, hard surface cleaners, wood products, plastic products or for any other antimicrobial applications where protection from microbes is required.

In accordance with another embodiment of the present invention, there is provided a coated substrate wherein the said substrate is coated with a synergistic antimicrobial composition comprising zinc pyrithione and zinc salt of pyridine carboxylic acid, their tautomeric forms, isomers, polymorphs, salts and solvates and mixtures thereof. The coated substrate of the present invention is selected from the group consisting of skin, hair, wood, metal, non-metal, plastic, wall and combinations thereof.

The present invention also provides a process for preparing the synergistic antimicrobial composition comprising zinc pyrithione and zinc salt of pyridine carboxylic acid, said process comprising mixing a slurry of zinc pyrithione in water and dispersant with a solution or suspension of zinc salt of pyridine carboxylic acid in a suitable solvent; adding the additional components to this slurry and mixing to obtain a homogenous suspension of antimicrobial composition. The mixing is done by the process known in the art to get the required particle size. The composition so prepared, in one embodiment of the invention is incorporated into various personal care, paint, coating, and other industrial formulations.

The personal care, paint or coating formulations are prepared by the processes known to the person skilled in the art.

Preferably, the antimicrobial combinations of this invention are incorporated into liquid compositions, especially dispersions of polymers in aqueous media. The biocide combinations are particularly useful in preservation of building materials, e.g., adhesives, caulk, joint compound, sealant, wallboard, paints, coatings, polymers, plastics, synthetic and natural rubber, paper products, fiberglass sheets, insulation, exterior insulating finishing systems, roofing and flooring felts, building plasters, wood products and wood-plastic composites. Preferably, the antimicrobial compositions are latex paints or other liquid coating compositions containing the biocide combinations disclosed herein. The biocide combinations are useful for preservation of the dry film coating resulting after application of a paint or other liquid coating composition. Preferably, the antimicrobial composition is an acrylic latex paint comprising one or more of the biocide combinations disclosed herein, or the dry film coating resulting from application of the paint to a surface.

The following examples are intended to illustrate, but in no way limit the scope of, the present invention.

EXAMPLES

Example 1

Preparation of Zinc Pyrithione-Zinc Salt Composition

Zinc pyrithione powder was mixed with water and dispersant in a high speed disperser (Part A). A solution/suspension of zinc salt of pyridine carboxylic acid was prepared by dissolving the salt in water disperser (Part B). The Part A and Part B were mixed thoroughly, followed by milling to obtain slurry of the required particle size. This slurry was mixed again with additional components to finally obtain a homogenous suspension of antimicrobial and/or biocidal composition. An exemplary composition obtained from the above process is tabulated below:

TABLE 1

Composition of transparent ZPTO-Zinc nicotinate stock

| Ingredients | Quantity % w/w | |
|---|---|---|
| ZPTO | 10.0% | 15.0% |
| Zinc salt | 10.0% | 15.0% |
| Water | 66.0% | 58.5% |
| Xanthum gum | 2.5% | 1.75% |
| Tamol NN 9104 | 2.0% | 1.5% |
| Propylene glycol | 9.25% | 8.0% |
| Preservative | 0.25% | 0.25% |

Example 2

Preparation of Personal Care Formulation

In a 250 ml capacity kettle (thick walled beaker), weighed amount of SLES (2EO), SLS (Galaxy 780) and water were taken and heated till 55° C. with stirring at 100 rpm to make a homogenous mixture. To this hot mixture, weighed amount of rheology modifier (Carbopol Aqua SF-1, Ultrez 20, Rheocare TTA, Xanthum gum etc.) was added slowly with continuous mixing. The turbid mixture thus obtained was neutralized either with amine or 0.1% NaOH solution. To this mixture, required amount of zinc pyrithione containing antimicrobial composition obtained in example 1 was added slowly and stirred continuously for 20-30 min to obtain a homogenous mixture. The pH of the system was maintained in the range of 6.5-8. Thereafter, CAPB was added at 40° C. followed by addition of glycerine, hydrovance and aqueous solution of Merquat 3330 (conditioner). After addition of all above mentioned ingredients, fragrance compatible with aqueous system was added to the system at room temperature. Total weight of kettle was taken and according to water loss, required amount of water was added. The mixture was stirred further for 10-15 min and was stored at room temperature in a container. Similarly, anti-microbial compositions comprising 40-50% ZPTO with ZnO and without any zinc salt and a blank composition (without ZPTO) and their shampoo formulations were prepared as described below.

TABLE 2

Hair care formulations

| Ingredients used (in % w/w) | 1 | 2 | 3 | 4 |
|---|---|---|---|---|
| SLES (2EO-28%) | 20.00 | 26.50 | 30.00 | 28.00 |
| SLS (28%) | 8.00 | 10.50 | 11.55 | 10.25 |
| DI Water | 53.00 | 39.75 | 37.00 | 40.50 |
| Ultrez 20 | — | — | 3.25 | 4.00 |
| Rheocare TTA | 6.00 | 5.00 | — | — |
| Zinc pyrithione-Zinc salt Mix | — | 2.00 | 1.00 | 0.50 |
| NaOH (10%) | 0.90 | 0.75 | 0.45 | 0.50 |
| CAPB | 6.00 | 6.50 | 8.00 | 7.00 |
| PEG 400 | 2.00 | — | 2.00 | — |
| Propylene Glycol | 2.35 | 4.00 | 2.00 | 4.00 |
| Sorbitol | — | 1.25 | 1.50 | 1.00 |
| Hydrovance | 1.00 | 2.00 | 2.00 | 2.00 |
| Merquat Plus 3330 | 0.50 | 1.50 | 1.00 | — |
| Colaquat CCG | — | — | — | 2.00 |
| Fragrance | 0.25 | 0.25 | 0.25 | 0.25 |
| Total formula | 100.00 | 100.00 | 100.00 | 100.00 |

Example 3

Preparation of Paint Formulation

In a 5000 ml capacity kettle, weighed amounts of DM water, propylene glycol, Dispex AA480 (dispersant), Triton CF 10 (non-ionic surfactant) were taken and mixed at 200-300 RPM for 10 minutes. To this mixture, ammonia solution (25%) as pH stabilizer (8.5-9.5) and Foamex 810 as defoamer were added, respectively. TT 4403 (thickener) dispersion in water (1:2) was added and mixed properly followed by addition of TiO$_2$ and Calcite powder (pigments) at 700-800 RPM. This grind phase was mixed for 30 minutes using a high-speed disperser. The grind phase paste was added to the Let-down phase premix prepared by mixing Acronal 295-D (resin) and Foamex 810 at 600-700 RPM. The antimicrobial composition comprising zinc pyrithione and zinc nicotinate as prepared in Example 1, and Texanol (Coalescent) were added and mixed for 10 minutes. To this mixture, Rheovis PU 1190 and aqueous dispersion of Rheovis AS 1125 (1:2) were added as rheology modifiers. This paint emulsion was mixed for another 30 minutes to obtain a paint formulation. The paint formulation was suitably applied to a wood substrate, and allowed to dry to form a dry coating. The dry film/coating exhibits excellent resistance to the growth of fungus and algae.

The anti-leaching activity of the paint formulation have been done as per ASTM method ASTM-D-6903-07. The studies were done using paint formulations comprising ZPTO as alone or in combination with various zinc salts (zinc oxide) or with zinc nicotinate. The data (average) for ZPTO concentration in artificial marine water and rate of biocide release are summarized in Table 4. The data clearly demonstrate that paint formulation with ZPTO and zinc nicotinate combination has reduced biocide release rate in comparison to paint formulations developed with ZPTO or ZPTO in combination with zinc salts ZnO.

The biocide (ZPTO) release rate in each test sample is calculated by the following formula:

Biocide (ZPTO) release rate = $(C_{ZPTO} * V * D)/(T * A)$ wherein, $C_{ZPTO}$=concentration of ZPTO in substitute ocean water ($\mu g L^{-1}$); V=substitute ocean water volume (L); D=hours per day; T=rotation period (hr); A=Area of paint ($cm^2$). The results of the biocide (ZPTO) release rate has been tabulated in table 4.

TABLE 3

Paint formulations

| Ingredients Used | Amount Taken (in % w/w) |
|---|---|
| Part 1 | |
| Water | 32.32 |
| Propylene Glycol | 2.20 |
| Dispex AA4480 | 3.00 |
| Triton CF 10 | 1.50 |
| Ammonia | 0.26 |
| Foamex 810 | 0.16 |
| TiO$_2$ | 13.00 |
| Calcite | 18.00 |
| TT 4403 | 1.00 |
| Attagel 50 | 1.00 |
| Part 2 | |
| Acronal 295 D | 24.00 |
| Foamex 810 | 0.16 |
| Rheovis PU 1190 | 1.00 |
| Rheovis AS 1125 | 0.50 |
| Zinc pyrithione-Zinc salt Mix | 0.60 |
| Texanol | 1.30 |
| Total formula | 100.00 |

TABLE 4

Biocide release rate (leaching) data of various ZPTO containing combinations

| Biocide Combination | ZPTO Conc (av.). ($\mu g L^{-1}$) | Rate of Biocide Leaching $(C_{ZPTO} * V*D)/(T*A)$ ($\mu g cm^2 d^{-1}$) |
|---|---|---|
| ZPTO | 2145.6 | 171.65 |
| ZPTO + ZnO | 4105.4 | 328.43 |
| ZPTO + ZnNIC | 915.6 | 73.25 |

(ZnNIC = Zinc Nicotinate)

Example 4

Antifungal/Anti-Dandruff Activity Studies

The anti-dandruff efficacy was determined by measuring zone of inhibition using disc diffusion method against *Malassezia furfur* (ATCC No. 14521). In this procedure, 10 μl of sample (zinc pyrithione and zinc salts combinations, stock compositions and shampoo formulations) was added on the filter paper disc and the disc was kept in the microbial culture swabbed on the culture media. The culture plates were incubated at 37° C. for 48 hrs and antifungal activity was evaluated by observing an area of no growth around the disc. An area of no growth around the swatch is known as a zone of inhibition. The anti-dandruff activity results against *M. furfur* for various zinc pyrithione and zinc salts combinations, zinc pyrithione -zinc nicotinate stock compositions and shampoo formulations are depicted in table 5 and 6. The synergistic anti-malassezia activity data based on synergy index for mixtures of zinc pyrithione (A) and zinc nicotinate (B) has been given in Table 6.

TABLE 5

Anti-dandruff activity data against *M. furfur* for various zinc pyrithione and zinc salts combinations
*M. furfur* activity data for various zinc salts with zinc pyrithione

| Test Conc. (w/w %) | | Zone of Inhibition (in mm) | | | | | | |
|---|---|---|---|---|---|---|---|---|
| ZnP | Zinc Salt | ZnP | Zn-Gly | ZnO | Zn-Glu | Zn-Lac | Zn-Nic | Zn-Pic |
| 0.25 | 0.25 | — | 30 | 30 | 38 | 38 | 40 | 35 |
| 0.25 | 0.50 | — | — | — | — | — | 40 | 38 |
| 0.25 | 1.50 | — | — | 32 | — | — | 38 | 38 |
| 0.50 | 1.50 | — | — | — | — | — | 48 | — |
| 1.00 | 0.25 | — | — | — | — | — | 32 | — |
| 1.00 | 0.50 | — | — | — | — | — | 48 | — |
| 0.25 | — | 30 | — | — | — | — | — | — |
| 0.50 | — | 30 | — | — | — | — | — | — |
| 1.00 | — | 30 | — | — | — | — | — | — |
| 1.50 | — | 30 | — | — | — | — | — | — |
| 2.00 | — | 30 | — | — | — | — | — | — |
| — | 0.25 | — | XX | XX | XX | XX | XX | XX |
| — | 0.50 | — | XX | XX | XX | XX | XX | XX |
| — | 1.00 | — | XX | XX | XX | XX | XX | XX |
| — | 1.50 | — | XX | XX | XX | XX | XX | XX |
| — | 2.00 | — | XX | XX | XX | XX | 6 | XX |
| DMSO Blank | XX | | | | | | | |
| O-Phosphoric Acid | XX | | | | | | | |
| Propylene Glycol | XX | | | | | | | |

Whereas XX denotes No Activity and (—) denotes Not Applicable or Not Tested

Synergy Index (SI)

The SI is calculated based on F. C. Kull et. al. method (Applied Microbiology, 1961, Vol. 9, 538). In this study, SI was calculated based on the following formula with the minimum inhibitory concentration chosen based on the percent inhibitory exhibited by the individual biocide against each microorganisms tested.

$$SI = Q_a/Q_A + Q_b/Q_B$$

$Q_a$=the concentration of compound A in the blend; $Q_b$=the concentration of compound B in the blend; $Q_A$=the concentration of compound A as the only biocide; $Q_B$=the concentration of compound B as the only biocide.

If SI (the Synergy Index) is greater than one, antagonism between the products is indicated. If the sum is equal to one, additivity is indicated. But when SI is less than one, synergism is shown, i.e. the lower the SI the greater the synergy shown.

TABLE 6

Synergistic Anti-malassezia activity of mixtures of zinc pyrithione (A) and zinc nicotinate (B)
Calculation of the synergy index of zinc pyrithione(A) and zinc nicotinate (B) with respect to *M. furfur*

| $Q_a$ | $Q_b$ | Total | $Q_a/Q_A$ | $Q_b/Q_B$ | $(Q_a/Q_A + Q_b/Q_B)$ = SI |
|---|---|---|---|---|---|
| 0 | 35000 ($Q_B$) | 35000 | 0.0 | 1.0 | 1.0 |
| 4 | 12500 | 12504 | 0.5 | 0.357 | 0.857 |
| 5 | 6250 | 6255 | 0.625 | 0.178 | 0.803 |
| 5 | 3125 | 3130 | 0.625 | 0.089 | 0.714 |
| 5 | 1562 | 1567 | 0.625 | 0.045 | 0.670 |
| 6 | 6250 | 6256 | 0.75 | 0.178 | 0.928 |
| 6 | 3125 | 3131 | 0.75 | 0.089 | 0.839 |
| 6 | 1562 | 1568 | 0.75 | 0.045 | 0.795 |
| 6 | 781 | 787 | 0.75 | 0.022 | 0.772 |
| 7 | 1562 | 1569 | 0.875 | .045 | 0.92 |
| 7 | 781 | 788 | 0.875 | 0.022 | 0.897 |
| 7 | 391 | 398 | 0.875 | 0.011 | 0.886 |
| 8 ($Q_A$) | 0 | 8 | 1.0 | 0.0 | 1.0 |

According to the data in Table 5 and 6, the SI values for ZPTO and Zinc nicotinate were found to be less than 1 which indicates synergistic behaviour of the antimicrobial actives in blended antimicrobial composition. This synergism leads to a lower level of usage and allows for fast action due to the synergetic combination of zinc pyrithione and zinc salt of pyridine carboxylic acid for sound antimicrobial properties While this invention has been described in detail with reference to certain preferred embodiments, it should be appreciated that the present invention is not limited to those precise embodiments rather, in view of the present disclosure, which describes the current best mode for practicing the invention, many modifications and variations, would present themselves to those skilled in the art without departing from the scope and spirit of this invention. This invention is susceptible to considerable variation in its practice within the spirit and scope of the appended claims.

We claim:

1. A synergistic antimicrobial composition comprising zinc pyrithione and a zinc salt of a pyridine carboxylic acid, their tautomeric forms, isomers, salts and solvates and mixtures thereof.

2. The synergistic antimicrobial composition as claimed in claim 1, wherein zinc pyrithione is present in an amount ranging from 0.01-50% w/w.

3. The synergistic antimicrobial composition as claimed in claim 1, wherein the zinc salt of a pyridine carboxylic acid is present in an amount ranging from 0.001-30% w/w.

4. The synergistic antimicrobial composition as claimed in claim 1, wherein the weight ratio of the zinc salt of a pyridine carboxylic acid to the zinc pyrithione is in the range from about 1:300 to about 50:1.

5. The synergistic antimicrobial composition as claimed in claim 1, wherein the zinc pyrithione have an average size of particle ranging from 0.1 microns to about 20 microns.

6. The synergistic antimicrobial composition as claimed in claim 1, wherein the composition is present in the form of or is incorporated into a personal care formulation or an industrial formulation.

7. The synergistic antimicrobial composition as claimed in claim 6, wherein the composition is present in an amount ranging from 0.001-10% w/w based on the total weight of the personal care formulation or the industrial formulation.

8. The synergistic antimicrobial composition as claimed in claim 6, wherein
the personal care formulation is selected from the group consisting of shampoos, creams, lotions, sprays, tonics, gels, paste, mousses, serums, oils, solid or liquid soaps, shower gels and hair conditioning and/or moisturizing compositions, hair strengthening compositions, hair drying compositions, hair coloring compositions, hair shaping compositions, hair dyeing compositions, face lotions, body lotions, moisturizing compositions, sun protection compositions, makeup preparations, shaving preparations and aids, hand cleansers, water-less hand sanitizer and facial cleansers, powders, anti dandruff and /or anti fungal hair care; and
wherein the industrial formulation is selected from the group consisting of coatings, paints, varnishes, stains, renders, lattices, polymer dispersions, adhesives, cleaning products, lignosulfonates, chalk slurries, mineral slurries, ceramic masses, adhesives, sealants, products containing casein, products containing starch, bitumen emulsions, surfactant solutions, motor fuels, cleaning products, pigment pastes, pigment dispersions, inks, lithographic fluids, thickeners, toiletries, water circuits, liquids associated with paper processing, liquids associated with leather making, liquids associated with textile production, drilling oils, cutting oils, hydraulic fluids, cooling lubricants, and in-can preservatives.

9. The synergistic antimicrobial composition as claimed in claim 1, further comprising one or more pyrithiones.

10. The synergistic antimicrobial composition as claimed in claim 9, wherein the one or more pyrithiones are selected from the group consisting of sodium pyrithione, silver pyrithione, copper pyrithione, iron pyrithione, aluminum pyrithione, calcium pyrithione, potassium pyrithione, magnesium pyrithione, barium pyrithione, and combinations thereof.

11. A synergistic antimicrobial composition comprising:
a) water,
b) a surfactant from the group consisting of anionic surfactant, cationic surfactant, non-ionic surfactant, amphoteric surfactants or a combination thereof,
c) zinc pyrithione, in an amount of from 0.01% to 2.0%, based upon the weight of the composition, and
d) a zinc salt of a pyridine carboxylic acid at a concentration of from 0.001% to 5%, based upon the weight of composition.

12. The synergistic antimicrobial composition as claimed in claim 11, further comprising one or more components selected from the group consisting of solubilizers, dispersants, rheology modifiers, suspending agents, diluents, humectants, pH regulators, preservatives, perfumes, skin active agents and/or scalp modifiers, hair growth agents, hair loss preventive agents, sunscreens, UV absorbers, vitamins and herbal extracts.

13. The synergistic antimicrobial composition as claimed in claim 1, further comprising:
water, and
a base medium comprising resin selected from the group consisting of vinyl, alkyl, epoxy, acrylic, polyurethane, polyester resins, and combinations thereof, wherein
the zinc pyrithione is present in an amount of from 0.01% to 5.0% based upon the weight of the composition, and
the zinc salt of a pyridine carboxylic acid is present at a concentration of from 0.001% to 10% based upon the weight of the composition.

14. The synergistic antimicrobial composition as claimed in claim 1, wherein the pyridine carboxylic acid is selected from the group consisting of 2-pyridinecarboxylic acid; 3-pyridine carboxylic acid; 4-pyridinecarboxylic acid; 2,3-pyridinedicarboxylic acid; 2,6-pyridinedicarboxylic acid; 2,5-pyridinedicarboxylic acid; 3,5-pyridinedicarboxylic acid, their tautomeric forms, isomers, polymorphs, salts and solvates and mixtures thereof.

15. The synergistic antimicrobial composition as claimed in claim 14, wherein the pyridine carboxylic acid is selected from the group consisting of 2-pyridinecarboxylic acid, 3-pyridinecarboxylic acid, their tautomeric forms, isomers, polymorphs, salts and solvates and mixtures thereof.

16. The synergistic antimicrobial composition as claimed in claim 13, wherein zinc salt of a pyridine carboxylic acid is present in an amount from 0.001 to 2%, based upon the weight of the composition.

17. A coated substrate wherein the substrate is coated with the synergistic antimicrobial composition as claimed in claim 1.

18. A coated substrate as claimed in claim 17 wherein the substrate is selected from the group consisting of skin, hair, wood, metal, non-metal, plastic, wall and combinations thereof.

19. The synergistic antimicrobial composition as claimed in claim 1, wherein the composition is present in the form of or is incorporated into any one of a personal care formulation, a hair care formulation, a skin care formulation, a medical formulation, a fabric care composition, a cutting oil, a coolant system, a paint, a coating, an adhesive, a caulk, a sealant, a wet-state preservative, a hard surface cleaner, a wood product and a plastic product.

20. The synergistic antimicrobial composition as claimed in claim 1, wherein the composition is present in the form of or is incorporated into anti dandruff hair care formulations.

21. The synergistic antimicrobial composition as claimed in claim 1, wherein the antimicrobial composition is any one of an antifungal composition, an antibacterial composition, and an antialgal composition.

22. The synergistic antimicrobial composition as claimed in claim 11, wherein the antimicrobial composition is any one of an antifungal composition, an antibacterial composition, and an antialgal composition.

* * * * *